US008618824B2

(12) United States Patent
Greegor et al.

(10) Patent No.: US 8,618,824 B2
(45) Date of Patent: Dec. 31, 2013

(54) MEMS BASED KELVIN PROBE FOR MATERIAL STATE CHARACTERIZATION

(75) Inventors: Robert B. Greegor, Auburn, WA (US); Richard H. Bossi, Renton, WA (US)

(73) Assignee: The Boeing Company, Chicago, IL (US)

( * ) Notice: Subject to any disclaimer, the term of this patent is extended or adjusted under 35 U.S.C. 154(b) by 752 days.

(21) Appl. No.: 12/277,116

(22) Filed: Nov. 24, 2008

(65) Prior Publication Data

US 2010/0127692 A1 May 27, 2010

(51) Int. Cl.
*G01R 31/20* (2006.01)

(52) U.S. Cl.
USPC ............... 324/754.05; 324/522; 324/207.25

(58) Field of Classification Search
USPC ....................... 324/754.01–754.11
See application file for complete search history.

(56) References Cited

U.S. PATENT DOCUMENTS

| 4,100,442 | A  | * | 7/1978  | Besocke ...................... 310/117 |
| 4,649,336 | A  |   | 3/1987  | Bindner et al. ................ 324/61 |
| 5,369,370 | A  | * | 11/1994 | Stratmann et al. ............. 324/663 |
| 7,202,691 | B2 | * | 4/2007  | Lagowski et al. ......... 324/754.21 |
| 2005/0134293 | A1 | * | 6/2005  | Sergoyan et al. ............. 324/662 |
| 2007/0164763 | A1 | * | 7/2007  | Park .............................. 324/758 |
| 2007/0175282 | A1 | * | 8/2007  | Fetzer et al. ..................... 73/649 |
| 2007/0239018 | A1 | * | 10/2007 | Fetzer et al. .................. 600/459 |
| 2008/0202245 | A1 | * | 8/2008  | Young .............................. 73/644 |
| 2009/0302835 | A1 | * | 12/2009 | Sun et al. ....................... 324/240 |

OTHER PUBLICATIONS

Baikie et al., "Low cost PC based scanning Kelvin probe", Review of Scientific Instruments, vol. 69, No. 11, Nov. 1998.

* cited by examiner

*Primary Examiner* — Arleen M Vazquez
(74) *Attorney, Agent, or Firm* — Caven & Aghevli LLC

(57) ABSTRACT

A device and method for monitoring the material health of a structure, providing a miniaturized MEMS Kelvin probe within a housing, wherein the Kelvin probe comprises a conductive plate formed of a stable metal and positioned substantially parallel to the structure; a piezoelectric vibrator for vibrating the conductive plate; and an electrical circuit connected to the conductive plate and the structure, wherein the conductive plate and the structure form a capacitor. The device is contained in one small, lightweight package that can be placed at one or more locations of interest. The sensor can be left in-place for continuous monitoring or for active testing at desired intervals, or be brought to the aircraft at desired intervals.

16 Claims, 3 Drawing Sheets

MEMS BASED KELVIN PROBE FOR MATERIAL STATE CHARACTERIZATION

FIELD

The present disclosure is generally related to a method and apparatus for non-destructive inspection and monitoring of structural health. The invention has particular utility for use in inspection and monitoring structural health of aircraft structural elements and will be described in connection with such utility, although other utilities are contemplated.

BACKGROUND

Structural health management is a critical function for mission readiness and cost effectiveness of aircraft operations. Traditionally structural health management has been implemented through scheduled maintenance programs with appropriate nondestructive inspection for defect detection in critical areas. While this approach has been effective in providing low risk of structural failure in flight, it reduces operational availability and incurs significant levels of cost performing inspections that most frequently find no defects.

To reduce the need for removing aircraft from service for periodic scheduled inspections, concepts related to condition based maintenance principles are being developed. Along with advanced prognosis techniques to evaluate and predict Structural Integrity, a significant reduction or elimination of the need for scheduled maintenance will improve fleet life cycle costs and increase the operational availability of aircraft. This approach is made possible by structural health monitoring.

Material state awareness for aircraft structure has traditionally been determined from the detection and measurement of cracks or other damage that represent significant structure feature changes. Normally these feature changes must be of sufficient size that standard nondestructive inspection methods such as ultrasound, radiography and eddy current can measure them. X-ray diffraction can be used to characterize residual stress and this is a measurement in tune with material property or state measurement. Some mode of ultrasound also can be used to return material properties such as Young's modulus.

Another way in which the material state may be determined is by measuring the work function, from which may be derived stress, strain, fatigue, corrosion, adsorption or desorption of molecular species, moisture, etc. Work function is a term applied to the amount of energy required to transfer electrons from the interior of one substance across an interface boundary into an adjacent area of space, commonly expressed in the units of electron-volts. An apparatus for determining work function that is known in the art is the Kelvin probe, the method of which is also called the dynamic capacitor method. Referring to FIG. 1, a Kelvin probe works by placing a conducting plate adjacent to a conductive surface to be tested, arranged as a parallel plate capacitor with a small spacing, on the order of hundreds of microns or even smaller. The conductive plate typically is made of a stable metal such as gold and thus serves as a reference. When an external electrical circuit is connected to the capacitor, a flow of electrons will pass through this circuit, and the electrochemical potentials of the conducting plate and metal surface are equalized thereby. The work function may be measured as an electro-static potential difference generated between the two surfaces equal to the difference between the work function of the respective surfaces. The electro-static potential between the two plates is given by $V_{cpd}=1/e(\phi_2-\phi_1)$, where $\phi_1$ and $\phi_2$ are the work functions of the metal surface and the conductive plate. Note that the work function is independent of the spacing between the two surfaces and the capacitance is dependent upon said spacing. Thus, a periodic vibration changing the distance between the plates at a frequency $\omega$ results in a current $i(t)=V_{cpd}\omega\Delta C \cos \omega t$, where $\Delta C$ is the change in capacitance. For the measurement of $V_{cpd}$, an additional backing voltage is applied between the plates until the current $i(t)$ goes to zero. This backing voltage is proportional to the work function difference of the two plates.

The relative work function measurement is very sensitive to any changes on the surface of the material and is a useful tool for structural health monitoring. If corrosion products are formed on the surface, or dislocation density changes due to fatigue occur then the work function will be altered. It has been demonstrated that even wear at very low loads that involves the absence of wear debris and/or wear scars, affects the work function. The change in surface potential is believed to be the result of chemical and structural changes in the first few nanometers of the sample. Hence a Kelvin Probe should be a very sensitive sensor for surface changes and health monitoring. See, for example, U.S. Pat. No. 4,649,336; Derik DeVecchio and Bharat Bhushan, "Use of a Nanoscale Kelvin Probe for Detecting Wear Precursors," Rev. Sci. Instrum. 69, 3618 (1998); Kenichi Takahata and Yogesh B. Gianchandani, "Bulk-Metal-Based MEMS Fabricated by Micro-Electro-Discharge Machining," Electrical and Computer Engineering, 2007; and I. D. Baikie and P. J. Estrup, "Low Cost PC Based Scanning Kelvin Probe," Rev. Sci. Inst. 69(11), 3903 (1998).

Structural health monitoring technology currently has several shortcomings relative to the principles of non-destructive inspection. Structural health monitoring has not been proven to have reliable damage feature resolution with acceptable detection rates and at acceptable weight and cost. Furthermore, both structural health monitoring and non-destructive inspection methods are limited in terms of providing direct measurement of material state and often require baseline information to justify heuristic techniques that search for localized changes from baseline states. Material state awareness is not only knowledge of structural features (such as flaw size or presence of a corrosive environment) but also the condition of the material and its ability to perform its designed function. To achieve these goals, sensors, their power requirements and wiring must be such that they can be justified when weight and performance are critical to mission effectiveness.

Prior art devices do not address the problem of determining the material state of an aircraft structure in-service. The existing solutions have difficulties with the size of the equipment for implementation. X-ray diffraction, for example, in field applications is cumbersome and slow. Ultrasound Young's modulus measurement represents only one characteristic of material property measurement. Existing Kelvin probe designs can measure material work functions, but are likewise large and cumbersome.

SUMMARY

The present disclosure provides a Microelectronic Mechanical Systems (MEMS) based Kelvin Probe which overcomes the aforesaid and other operational difficulties of the prior art methods and devices by providing a small, lightweight device that can be incorporated on the aircraft for measuring a basic material characteristic of interest. The MEMS Kelvin Probe contains the sensor and electronics in one small, lightweight package that can be placed at locations of interest. The sensor can be left in-place for continuous monitoring or for active testing at desired intervals, or be brought to the aircraft at desired intervals.

In one aspect, the present disclosure provides a device for monitoring the material health of a structure, e.g., the skin, comprising a miniaturized MEMS Kelvin probe within a housing, wherein the Kelvin probe comprises: a conductive plate formed of a stable metal and positioned substantially parallel to the structure; a piezoelectric vibrator for vibrating the conductive plate; and an electrical circuit connected to the conductive plate and the structure, wherein the conductive plate and the structure form a capacitor.

In another aspect, the present disclosure provides a method for monitoring the structural health of a structural component, using a miniaturized Kelvin probe, the method comprising: attaching the Kelvin probe on the surface of the structural component; monitoring the work function of the structural component with the Kelvin probe; and generating an alarm when the work function of the structural component reaches or exceeds a pre-determined value.

Other systems, methods, features, and advantages of the present disclosure will be or become apparent to one with skill in the art upon examination of the following drawings and detailed description. The features, functions and advantages that have been discussed can be achieved independently in various embodiments of the present disclosure or may be combined in yet other embodiments further details of which can be seen with reference to the following description and drawings.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

The present disclosure provides a method and device employing a very small Kelvin probe that can be used for the measurement of the material state of an aircraft, in particular the surface work function, which is the amount of energy necessary to remove an electron from the surface. A measurement of the work function contains important information about the surface state. Many factors can influence the work function including stress, strain, fatigue, corrosion, adsorption or desorption of molecular species, moisture etc.

An essential element of the Microelectronic Mechanical Systems (MEMS) device is the micro mechanically mounted capacitive plate, standoff control to the surface, and, vibration and signal amplification circuitry all packaged in the small sensor device. The sensor is preferably constructed using silicon based MEMS technology with appropriate coating materials.

The sensor acts as two conductors arranged as a parallel plate capacitor using one plate in the MEMS and the test surface as the other plate. A piezoelectric driven periodic vibration of the distance between the plates results in a voltage that is related to a change in work function. The capacitor and electronics are built into the MEMS sensor.

Figure 1:
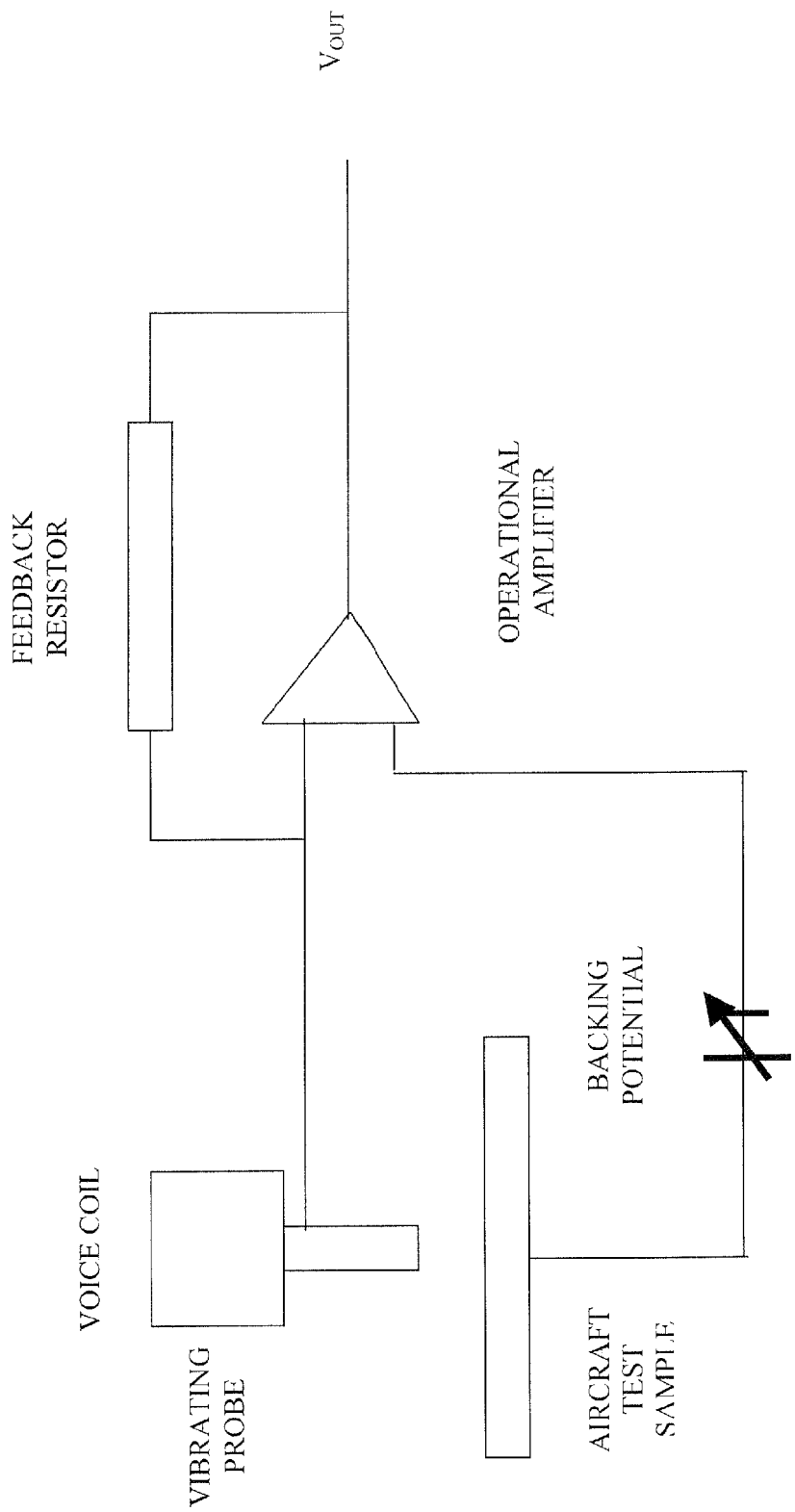
FIG. 1 is an illustration of a Kelvin probe.
Figure 2:
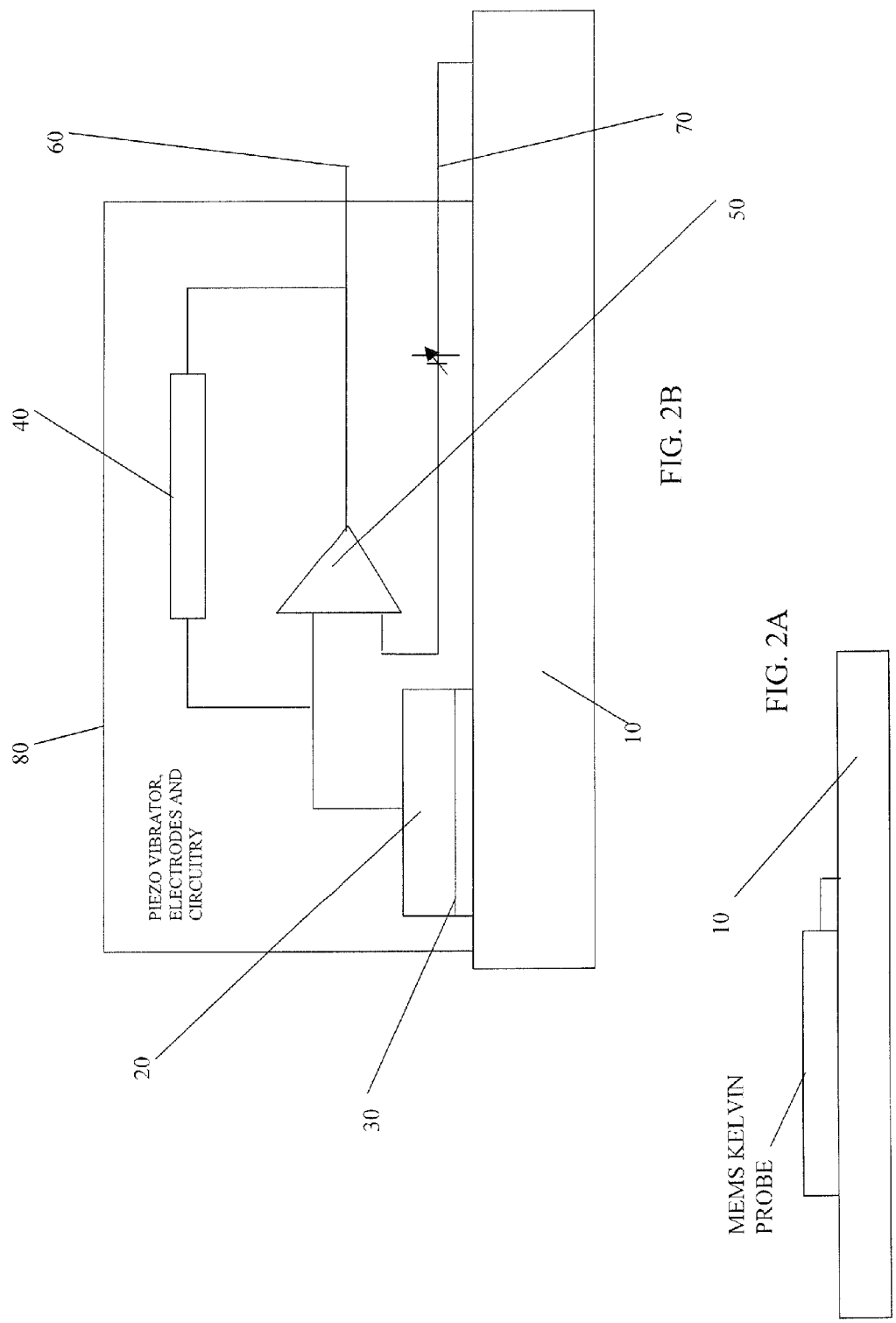
FIGS. 2A and 2B are illustrations of a Microelectronic Mechanical Systems (MEMS) based Kelvin probe, in accordance with the present disclosure.

The Kelvin probe of the present disclosure is miniaturized using MEMS technology. See FIGS. 2A and 2B. MEMS devices are typically between 20 μm and 1 mm in overall size, but the Kelvin probe discussed herein may further be useful at sizes as large as 1 cm and larger. This miniaturization is possible by replacing the voice coil of the prior art Kelvin probe with a piezoelectric device 20. A stable metal, such as gold, may be deposited on the surface of the piezoelectric device by sputtering, electroplating, chemical vapor deposition, or other known techniques for deposition of metals.

The feedback loop with resistor 40 and the required operational amplifier 50 are already small but may be manufactured to minimal size using techniques that are commonly used in semiconductor manufacturing. Similar techniques may be employed to optimize the size and functionality of the output connector 60 and backing potential connector 70. The various parts can be integrated into a package or housing 80 that is small, e.g., having a largest dimension of less than about 1 cm, lightweight and requires little power since only one small gold electrode needs to vibrate at micron displacements.

Figure 3:
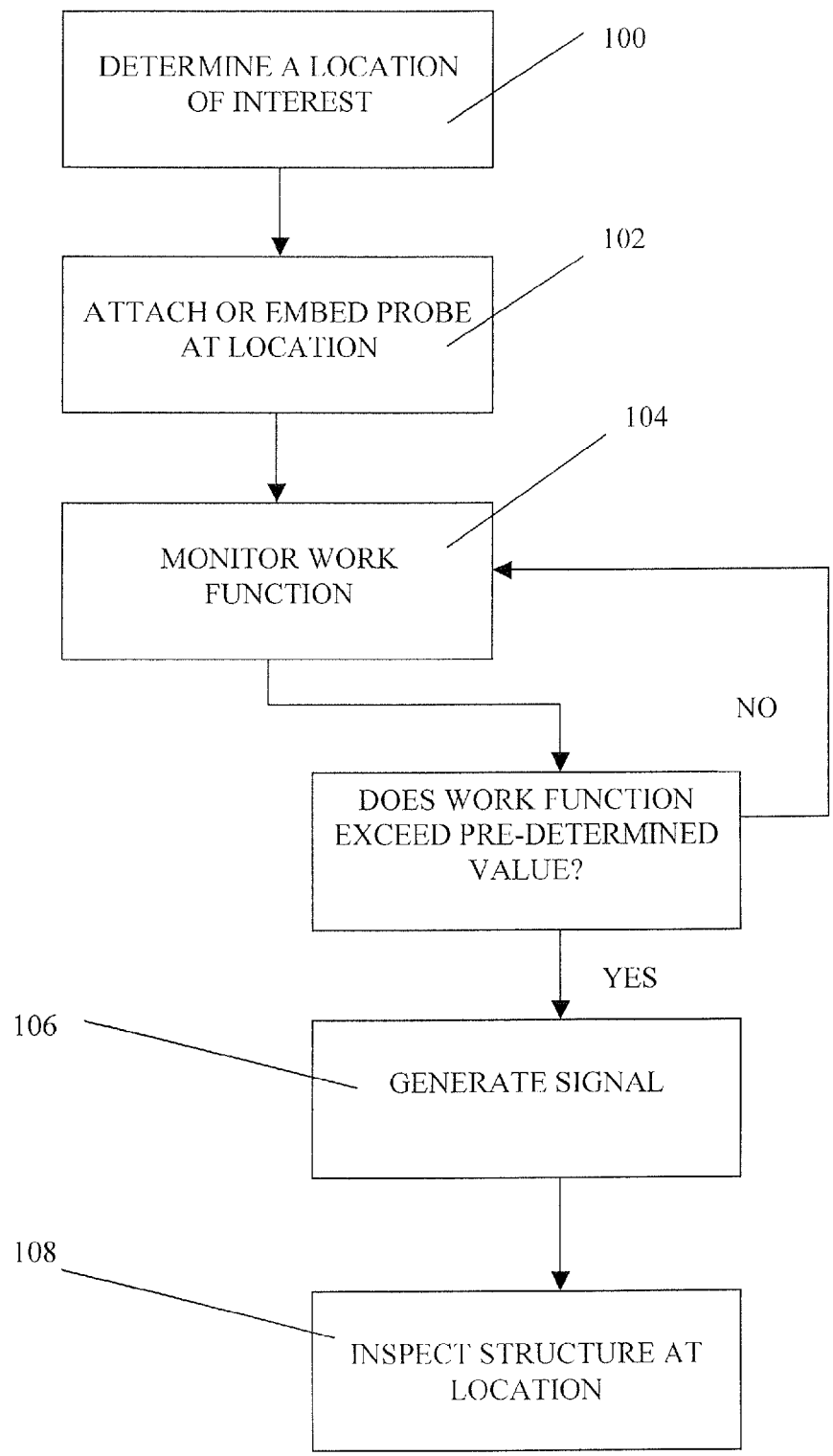
FIG. 3 is a flowchart displaying a method for structural health monitoring using a MEMS based Kelvin probe, in accordance with the present disclosure.

Referring to FIG. 3, the present disclosure also provides a method for structural health monitoring utilizing the above described MEMS based Kelvin probe. The method generally comprises the steps of determining a location of interest on a structure 100, attaching the Kelvin probe on the surface of a structure to be monitored 102; monitoring the work function of the structural component with the Kelvin probe 104; and generating an alarm when the work function of the structural component reaches or exceeds a pre-determined value 106; and, inspecting the structure 108.

The pre-determined value is chosen according to the known properties of the material forming the structure. No baseline data is required since only the readout of the relative work function of the surface is needed. When the work function value exceeds a pre-determined parameter, a signal would be activated indicating a structural health monitoring event in the area where the sensor was located. Upon receiving a signal that a structural health monitoring event has occurred, further inspection may be directed to the specific area where the signal originated.

Preferably, the MEMS based Kelvin probe of the present disclosure is integrated into regions of an aircraft structure 10 (see FIG. 2a) where corrosion or fatigue is expected to occur. Alternatively, the Kelvin probe described herein may be applied to various regions of interest periodically.

Further, monitoring of the work function may be continuous or intermittent. For example, where a Kelvin probe as described above has been attached or embedded in a region of an aircraft structure where corrosion is likely to occur, such as the skin of the aircraft. An external device, providing a power source for the piezoelectric vibrator and a means for reading the work function of the probe, may be used to obtain measurements from the attached or embedded probe during other scheduled maintenance for the aircraft. In this manner, the size of the device may be optimized by eliminating the need for a power source. In addition, the work function may be measured quickly and accurately without unnecessary reduction in operational availability of the aircraft.

The MEMS based Kelvin Probe described herein would overcome the operational difficulties of the other methods by providing a small, lightweight device that can be incorporated on the aircraft for measuring a basic material characteristic of interest. The MEMS Kelvin Probe contains the sensor and electronics in one small, lightweight package that can be placed at one or more locations of interest. The sensor can be left in-place or attached to the structure for continuous monitoring or for active testing at desired intervals, or be brought to the aircraft at desired intervals.

It should be emphasized that the above-described embodiments of the present disclosure, particularly, any "preferred" embodiments, are merely possible examples of implementations, merely set forth for a clear understanding of the principles of the present disclosure. Many variations and modifications may be made to the above-described embodiments without departing substantially from the spirit and principles of the disclosure. For example, the device and method of the present disclosure have been described above in connection with structural health monitoring of an aircraft surface, but other uses, such as monitoring the structural health of a building component, railway system, or other system where structural health and operational availability are at issue, are also possible. All such modifications and variations are intended to be included herein within the scope of this disclosure and protected by the following claims.

What is claimed is:

1. A device for monitoring the material health of a structure, comprising a miniaturized MEMS Kelvin probe within a housing, wherein the Kelvin probe comprises:
    a conductive plate disposed entirely within the housing and formed of a stable metal and positioned substantially parallel to the structure, wherein the structure is outside the housing;
    a piezoelectric vibrator coupled to the conductive plate for vibrating the conductive plate relative to the structure, wherein the piezoelectric vibrator comprises edges and the conductive plate does not extend beyond the edges of the piezoelectric vibrator; and
    an electrical circuit connected to the conductive plate and the structure, wherein the conductive plate and the structure form a capacitor.

2. The device of claim 1, wherein the electrical circuit comprises:
    an operational amplifier;
    a feedback loop;
    a backing connection connecting the electrical circuit to the structure; and
    an output connection.

3. The device of claim 1, wherein the conductive plate is formed by sputtering, chemical vapor deposition, or electroplating.

4. The device of claim 3, wherein the conductive plate is formed on the surface of the piezoelectric vibrator.

5. The device of claim 1, wherein the electrical circuit is formed using semiconductor manufacturing techniques.

6. The device of claim 1, wherein the structure is an aircraft.

7. The device of claim 6, wherein the structure comprises a skin of an aircraft.

8. The device of claim 1, wherein the largest dimension of the housing is less than 1 cm.

9. The device of claim 1, wherein the housing is attached in the structure.

10. A method for monitoring the structural health of a structural component, using a miniaturized MEMS Kelvin probe, the method comprising:
    attaching the Kelvin probe on the surface of the structural component, wherein the Kelvin probe comprises:
        a conductive plate disposed entirely within a housing and formed of a stable metal and positioned substantially parallel to the structure, wherein the structural component is outside the housing;
        a piezoelectric vibrator coupled to the conductive plate for vibrating the conductive plate relative to the structure, wherein the piezoelectric vibrator comprises edges and the conductive plate does not extend beyond the edges of the piezoelectric vibrator; and
        an electrical circuit connected to the conductive plate and the structure, wherein the conductive plate and the structure form a capacitor;
    monitoring a work function of the structural component with the Kelvin probe; and
    generating an alarm when the work function of the structural component reaches or exceeds a pre-determined value.

11. The method of claim 10, wherein the structural component is an aircraft structure.

12. The method of claim 11, wherein the structural component comprises a skin of an aircraft.

13. The method of claim 10, wherein the monitoring of the work function is continuous.

14. The method of claim 10, wherein the monitoring of the work function is intermittent.

15. The method of claim 10, further comprising inspecting the structural component when an alarm is detected.

16. The method of claim 10, wherein the step of attaching the Kelvin probe is preceded by determining a location of interest on the structural component.

* * * * *